United States Patent
Core et al.

(10) Patent No.: US 9,707,114 B2
(45) Date of Patent: Jul. 18, 2017

(54) STENT DELIVERY SYSTEM

(71) Applicant: 480 Biomedical, Inc., Watertown, MA (US)

(72) Inventors: Lee Core, Needham, MA (US); Travis White, Zimmerman, MN (US); Tristan Tieso, Fridley, MN (US); Brady Hatcher, Rogers, MN (US); Joe Lesser, Maple Grove, MN (US); Emily Rusk, Boston, MA (US); Randall James Beyreis, Corcoran, MN (US)

(73) Assignee: 480 BIOMEDICAL, INC., Watertown, MA (US)

( * ) Notice: Subject to any disclaimer, the term of this patent is extended or adjusted under 35 U.S.C. 154(b) by 679 days.

(21) Appl. No.: 14/035,252

(22) Filed: Sep. 24, 2013

(65) Prior Publication Data

US 2014/0094895 A1   Apr. 3, 2014

Related U.S. Application Data

(63) Continuation-in-part of application No. 13/606,962, filed on Sep. 7, 2012, now Pat. No. 9,198,783, which is a continuation-in-part of application No. 12/573,687, filed on Oct. 5, 2009, now Pat. No. 8,372,133.

(51) Int. Cl.
| | | |
|---|---|---|
| *A61F 2/06* | (2013.01) | |
| *A61F 2/966* | (2013.01) | |
| *A61F 2/90* | (2013.01) | |
| *A61F 2/86* | (2013.01) | |
| *A61F 2/82* | (2013.01) | |
| *A61F 2/95* | (2013.01) | |

(52) U.S. Cl.
CPC ............ *A61F 2/966* (2013.01); *A61F 2/90* (2013.01); *A61F 2/86* (2013.01); *A61F 2002/826* (2013.01); *A61F 2002/9505* (2013.01); *A61F 2002/9522* (2013.01); *A61F 2002/9665* (2013.01); *A61F 2230/005* (2013.01); *A61F 2230/008* (2013.01); *A61F 2230/0054* (2013.01); *A61F 2230/0067* (2013.01)

(58) Field of Classification Search
CPC .... A61F 2/90; A61F 2/966; A61F 2/86; A61F 2230/0054; A61F 2002/826; A61F 2002/9505; A61F 2002/9522; A61F 2002/9665
See application file for complete search history.

(56) References Cited

U.S. PATENT DOCUMENTS

2008/0183272 A1 * 7/2008 Wood ................. A61F 2/95 623/1.11

* cited by examiner

*Primary Examiner* — Ashley Fishback

(57) ABSTRACT

Delivery systems for polymeric tubular implants, kits that include such delivery systems, and methods of treating patients by implanting tubular implants using the delivery systems. The delivery systems include an inner shaft, an expandable member slidably disposed about the inner shaft and configured to receive the tubular implant, and a tubular outer shaft disposed about the inner shaft.

16 Claims, 16 Drawing Sheets

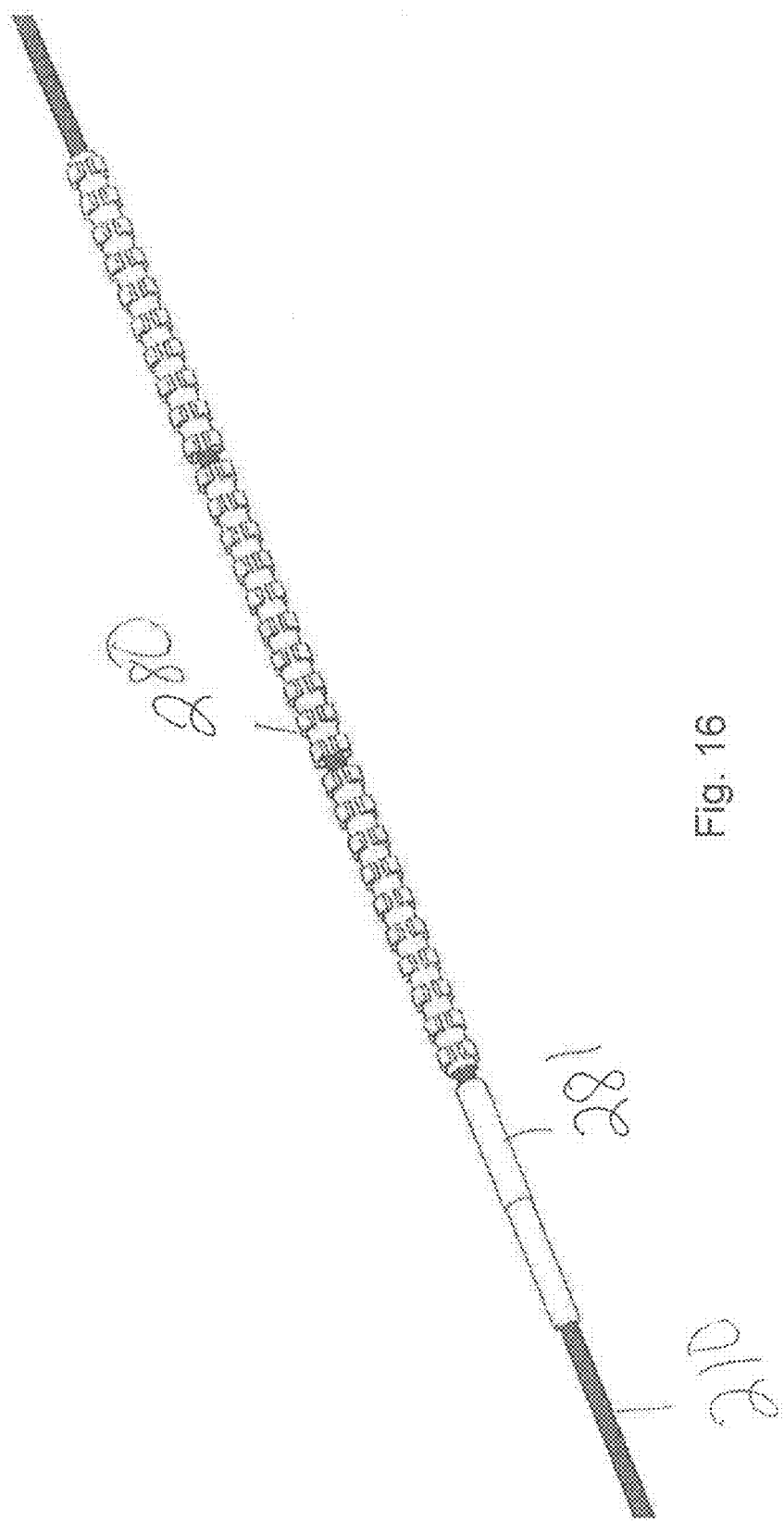

STENT DELIVERY SYSTEM

CROSS-REFERENCE TO RELATED APPLICATIONS

This Application is a continuation-in-part of currently pending U.S. patent application Ser. No. 13/606,962, titled "Polymeric Implant Delivery System" by Nareak Douk, et al. (Douk II), which is a continuation-in-part of U.S. application Ser. No. 12/573,687, also titled "Polymeric Implant Delivery System" by Nareak Douk, et al., now U.S. Pat. No. 8,372,133 (Douk I). The entire disclosure of each of the foregoing references is hereby incorporated by reference for all purposes.

FIELD OF THE INVENTION

The present invention relates to devices and methods used to deliver polymeric tubular implants to patients in need thereof.

BACKGROUND

A variety of medical conditions can be treated by implanting tubular devices into natural body lumens. For example, it is commonplace to implant metallic stents into the coronary arteries of patients with heart disease following balloon angioplasty to minimize the risk that the arteries will undergo restenosis. Recently, commercial stents have included drug-eluting polymer coatings that are designed to further decrease the risk of restenosis. Other examples of conventional tubular medical implants include woven grafts and stent-grafts that are used to span vascular aneurysms, polymeric tubes and catheters that are used to bypass strictures in the ureter and urethra, and stents that are used in the peripheral vasculature, prostate, and esophagus.

Despite the evolution of metallic stents, they continue to have limitations including potentially causing thrombosis and vascular remodeling. While biostable and biodegradable polymeric stents have been proposed to address the limitations of metallic stents, their use has been limited by a number of factors. Among these is the fact that polymeric stents are generally not as strong as their metallic counterparts, and they may undergo stress relaxation if left in a crimped delivery configuration for an extended period of time, such as during shipping and storage. In addition, many conventional stent delivery systems, particularly for self-expanding stents, grasp the stent at isolated locations or otherwise place localized stresses on the stent. For polymeric stents, this presents the possibility that the polymer becomes permanently deformed or otherwise damaged at these locations.

Another problem affects both metallic and polymer stents: a stent can move laterally as it is released from the delivery system, a phenomenon termed "stent jumping," which may result in damage to the stent or incorrect placement, which in turn may injure the patient.

The applicants have previously described, in Douk I and II, a delivery system that can be used to deliver polymeric tubular implants, such as stents, into a lumen of a patient that minimizes the risk of stent-jumping. And, because the delivery systems of Douk I and II can be loaded with tubular implants by a user or operator in-suite just prior to implantation, the risk that the implant will undergo stress relaxation during shipping and/or storage in a loaded or crimped configuration is also minimized.

Exemplary delivery systems according to Douk I and II generally include (i) an inner shaft that comprises a distal end configured for insertion into a patient, with at least a portion of the inner shaft having an outer diameter less than an inner diameter of a crimped polymeric tubular implant; (ii) an expandable member that is slidably disposed about the inner shaft and includes an open distal end with a cross-sectional dimension that is greater than the diameter of the un-crimped polymeric tubular implant, so that at least part of the polymeric tubular implant when in an unstressed configuration can be inserted into the open distal end; and (iii) a tubular outer shaft slidably disposed over the inner shaft and the expandable member. In use, delivery devices according to Douk I and II are loaded, optionally with the aid of a loading device described below, as follows: the tubular outer shaft is retracted to expose the distal end of the inner shaft, a polymeric tubular implant is positioned around the inner shaft and the expandable member is moved to encompass at least part of the polymeric tubular implant. Finally the tubular outer shaft is advanced toward the distal end to compress the expandable member, compressing and crimping the polymeric tubular implant. The expandable member is then retracted away from the implant, leaving it ready for deployment.

To deploy a polymeric tubular implant using a device of Douk I and II, the distal end of the device is inserted into a body lumen, such as a blood vessel, and positioned at a the outer shaft is retracted away from the distal end of the inner shaft to expose the polymeric tubular implant, allowing it to expand into an unstressed shape and to make contact with the inner wall of the body lumen. A device according to Douk I and II optionally includes a second expandable member that is positioned or positionable distally to the tubular implant so that, during deployment, it can be expanded to provide a barrier to migration, then retracted to permit removal of the device from the body.

The devices described in Douk I and II reduce the likelihood of damage or mis-placement of polymeric stents, but there is a constant need in the medical device field for improvements in ergonomics, usability, safety and efficacy.

SUMMARY OF THE INVENTIONS

The present invention improves on the devices of Douk I and II by providing, in one aspect, a kit that, in certain embodiments, includes a tray containing an implant, a loading aid, and a delivery catheter. The implant is provided in an uncompressed, relatively larger diameter configuration within a through-lumen of the loading aid, which in turn rests in an elongate space within the tray. The delivery catheter includes an inner shaft, a first expandable member that slides about the length of the inner shaft, and an outer sheath that slides over both the inner shaft and the first expandable member. The distal tip of the catheter, which is configured to contain the implant in a compressed, smaller diameter configuration, is positioned in the elongate space with the loading aid, and the inner shaft of the delivery device lies on the same axis as the through-lumen of the loading aid and the tubular implant. The first expandable member includes a distal end that is sized and shaped to contain at least part of the implant.

In various embodiments, the delivery catheter includes a handle, which is positioned in a second space within the tray, and the kit is arranged so that, if the handle is removed from the second space, it does not result in displacement of the distal tip within the elongate space, the kit also includes a removable collar attached to the implant which interfits with the loading aid and which is also positioned in the elongate space, and the collar, the loading aid, and the elongate space, all have substantially the same width.

In another aspect, the invention provides a method for loading an implant onto a delivery catheter, embodiments of which include providing a kit as described above, connecting the loading and the collar within the elongate space, and advancing the inner shaft and the first expandable member into the through-lumen of the loading aid so that the inner shaft extends through the lumen of the implant while at least part of the implant lies within the first expandable member. The outer sheath is then advanced over both the first expandable member and the inner shaft, thereby crimping the tubular implant into a compressed configuration about the inner shaft. In some embodiments, the inner shaft can include a retentive cushion that is made from a compliant material, in which case the inner shaft is advanced so that the cushion is positioned within the lumen of the tubular implant, and the method can include removing the distal tip of the delivery device from the loading device and the collar.

In yet another aspect, the invention provides a device for delivering a compressible tubular implant to a patient that includes, in its various embodiments, an inner shaft with a distal end that can be inserted into a patient and a proximal end that remains outside of the patient, a first expandable member that slides about the length of the inner shaft and that has an open distal end that has a diameter greater than or equal to a first, unstressed diameter of the implant so that at least part of the implant can be placed within the first expandable member, and a proximal end that has a diameter less than the first diameter. The device also includes an outer sheath that slides over the first expandable member and the inner shaft. In certain embodiments the delivery device includes a cushion disposed about the inner shaft that includes a compliant material and has a repeating pattern of protrusions, which cushion may have a length between about 20% and 80% of the length of the stent. The distal end of the first expandable member has, in some cases, a region that has a constant diameter which is larger than the first diameter of the implant, and which is optionally made with a mesh or woven material that is characterized by nodes where structural elements of the mesh or weave intersect or overlap, and where the node density of the proximal portion of the first expandable member is greater than the node density in the constant diameter portion.

BRIEF DESCRIPTION OF THE DRAWINGS

FIG. 16 includes a schematic depiction of a cushion according to an embodiment of the invention.

DETAILED DESCRIPTION OF THE PREFERRED EMBODIMENTS

Delivery Devices

The present invention provides devices, methods, and kits used to deliver polymeric tubular implants to patients in need thereof without undue risk of damaging the implant during the delivery process. The tubular implants are generally used for implantation into small diameter bodily lumens, such as those found in the vascular, biliary, urogenital, gastrointestinal, and tracheal-bronchial anatomy. As is known in the art, such implants are dimensioned according to their intended application and placement location, and are generally several millimeters in diameter, and several millimeters to several tens of millimeters in length. They are formed by any suitable configuration, such as woven strands, loose braids, or unitary frameworks having a repeating or non-repeating pattern, as is known in the art.

Figure 1:
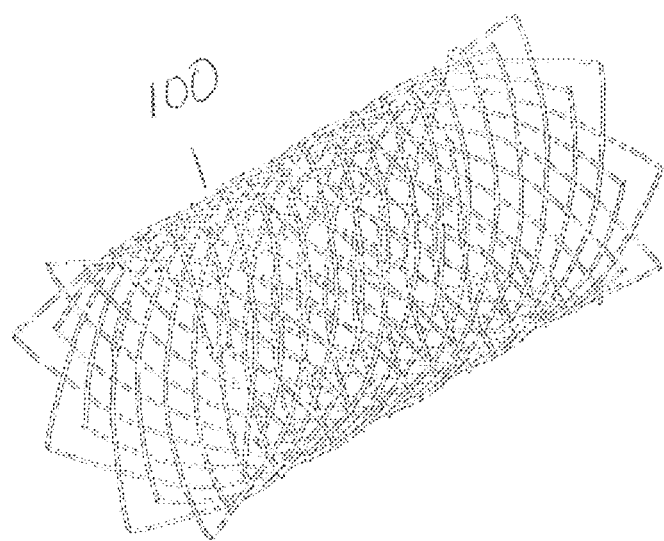
FIG. 1 is a perspective view of a polymeric tubular implant that may be delivered using the kits, systems and methods of the present invention.

A representative polymeric tubular implant 100 that may be delivered by the delivery system of the present invention is shown in FIG. 1. The implant 100 is manufactured to have an unstressed configuration, which is characterized by a certain diameter when not acted upon by external stresses. To deliver the implant 100 to a bodily lumen, it is compressed or "crimped" to a reduced diameter, inserted into the lumen using a delivery device, and then released from the delivery device. The implants used with the delivery system of the present invention are "self-expanding" such that when they are released from a delivery device, they will tend to expand towards their unstressed configuration without the aid of expansion means such as an expansion balloon. Preferably, the diameter of the bodily lumen is less than the diameter of the implant in its unstressed configuration so that the self-expanding nature of the implant results in the securement of the implant against the lumen wall by a slight pressure.

Figure 2:
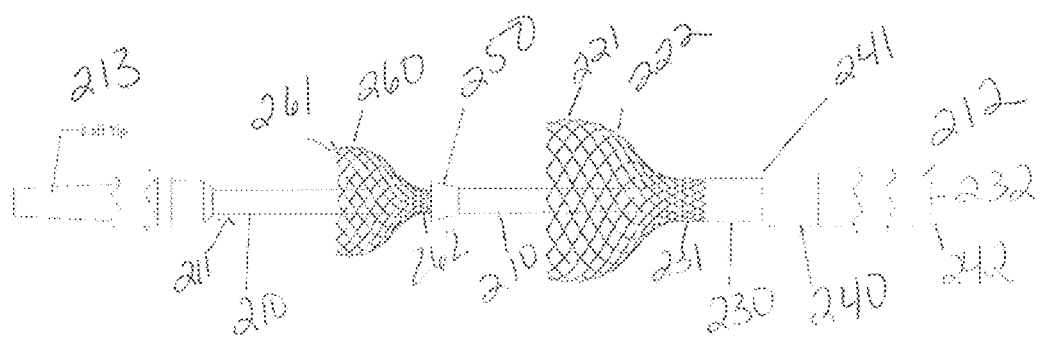
FIG. 2 is a side view of an exemplary delivery device.

One embodiment of the delivery system of the present invention is shown in FIG. 2. The delivery system 200 comprises an inner shaft 210 having distal end 211 configured for insertion into the lumen of a patient and a proximal end 212 configured to remain outside of the patient when the distal end 211 is inserted into the patient. The inner shaft 210 is stiff enough to provide sufficient structural integrity to be pushed through bodily lumens, and is made from any suitable material such as, for example, a biocompatible reinforced or non-reinforced polymer material such as a polyimide, polyamide, high density polyethylene (HDPE), or polyetheretherketone (PEEK). Preferably, a soft tip 213 is connected to the distal end 211 of the inner shaft 210 so to minimize risk of damage to the walls of a bodily lumen during insertion of the delivery system 200. In some cases, the inner shaft 210 and the soft tip 213 define a contiguous through-lumen for insertion of a guidewire, to permit over-the-wire positioning of delivery systems of the invention.

Delivery system 200 includes a first expandable member 220 slidably disposed about the inner shaft 210. In one embodiment, the first expandable member 220 is connected to the distal end 231 of a tubular middle shaft 230, which is slidably disposed about the inner shaft 210 by manipulation of the tubular middle shaft 230 at its proximal end 232. The tubular middle shaft 230 is made from any suitable material that allows it to flex to follow the configuration of the inner shaft 210 as the tubular middle shaft 230 slides over the inner shaft 210. Examples of such materials include, for example, biocompatible reinforced or non-reinforced polymer materials such as polyimides, polyamides, and HDPE.

The first expandable member 220 is a resilient structure that, when not subjected to external stresses, will self-expand to an unstressed configuration such as the configuration shown in FIG. 2. First expandable member 220 may be made from any suitable metallic or polymeric material, and is preferably a shape memory material such as Nitinol. If first expandable member 220 is not made from a shape memory material, it is made from an otherwise elastic material having a configuration that results in a self-expanding property, such as, for example, spring temper stainless steel or cobalt nickel alloys. Preferably, the first expandable member has a mesh or woven structure, as shown in FIG. 2.

Figure 3:
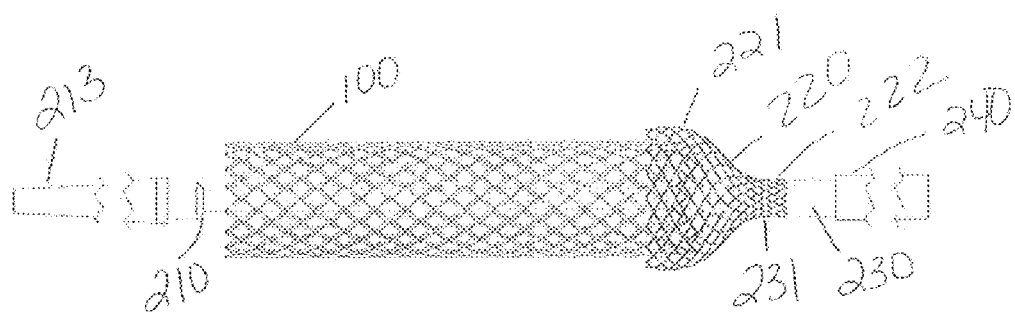
FIG. 3 is a side view of a delivery device during loading of a polymeric tubular implant, in accordance with an embodiment of the present invention.

The first expandable member 220 has an open distal end 221 when in an unstressed configuration. The cross-sectional dimension of the open distal end 221 is greater than the diameter of the implant 100 in its unstressed configuration such that at least a portion of the implant 100 may be placed therein, as shown in FIG. 3. In a preferred embodiment, the proximal end 222 of first expandable member 220 is connected to the distal end 231 of tubular middle shaft 230 using an adhesive or any suitable mechanical attachment means, as previously described. The primary function of the first expandable member 220 is to provide a means of crimping the tubular implant 100 into a reduced configuration to facilitate delivery and placement within a bodily lumen. This action is accomplished by the relative advancement of a tubular outer shaft 240, which is slidably disposed about the inner shaft 210 (and if used, the tubular middle shaft 230), distally such that the tubular outer shaft 240 compresses the first expandable member 220 as it slides over the first expandable member 220. Because at least a portion of the implant 100 is placed within the open distal end 221 of the first expandable member 220, the implant 100 is likewise compressed by the first expandable member 220 as the tubular outer shaft 240 slides over the first expandable member 220. Preferably, and as shown in FIG. 2, the open distal end 221 of first expandable member 220 is circular such that when it compresses the implant 100, it applies a substantially uniform radial force along the circumference of the implant 100 and does not result in the application of any significant stress concentration locations that result in the permanent deformation of the implant 100.

The tubular outer shaft 240 is made from any suitable material that allows it to achieve its intended functions. Preferably, the tubular outer shaft 240 is characterized by a low coefficient of friction to allow for ease of loading and deployment of the implant 100 as described herein. For example, the tubular outer shaft 240 is preferably made from a material such as fluorinated ethylene propylene (FEP) or polytetrafluoroethylene (PTFE), or is coated with a lubricious coating as is known in the art. The coating is preferably applied to both the inner and outer surfaces of the outer shaft 240, to permit it to slide smoothly over both the inner shaft 210 and the first expandable member 220 as well as through the body lumen into which the device 200 is positioned.

The tubular outer shaft 240, as well as the inner shaft 210 and the optional middle shaft 230, has a length sufficient to permit the distal portion of the device to be inserted into a patient and threaded through potentially tortuous blood vessels to reach an implantation site. For instance, the device 200 may be configured so that a portion having a length of approximately 120 centimeters is available for insertion into a body and/or to provide slack between the portion within the body and the handle of the device when used by an end user of the delivery device 200.

Additionally, the tubular outer shaft 240 is preferably relatively stiff, to help the outer shaft 240 to resist kinking, and to improve the pushability of the delivery device 200. In some embodiments, the tubular outer shaft includes a braided material along all or part of its length, which braided material provides improved stiffness relative to non-braided catheter materials.

Delivery devices of the invention are generally compatible with guidewires, introducer sheaths and other accessories currently used in the art for introducing catheters into the body. In various embodiments, delivery devices of the invention have varying dimensions to permit loading and delivery of implants in a variety of lengths (e.g. 40 mm, 80 mm, 100 mm) and can be introduced using a 7 F introducer sheath and a 0.018" guidewire.

The First Expandable Member

The first expandable member 220 is preferably shaped to include a section having an inner diameter which gradually increases from the proximal end 222 to distal end 221 so that, when the first expandable member 220 is engaged with a tubular implant 100 a gradual compressive force is applied to the implant 100 as the outer shaft 240 is advanced over the first expandable member 220. As shown in FIG. 2, and as discussed in Douk I and II, a preferred shape for the first expandable member 220 is similar to a funnel. The inventors have found that short, funnel shaped members that include a distal section having a more or less constant inner diameter when expanded (a "capture flare"), such as those shown in FIGS. 17B and 18A-B, advantageously engage and capture tubular implants without displacing them. In these embodiments, when the tubular implant 100 is engaged with the first expandable member 220 and compressed, the constant diameter portion of the first expandable member 220 advantageously applies a compressive force that is substantially normal to (perpendicular to) the outer surface of the expanded tubular implant 100. By contrast, longer first expandable member designs and designs that incorporate a substantially constant taper over most of their length, apply forces both normal and parallel to the surface of the tubular implant 100, promoting displacement.

Figure 8:
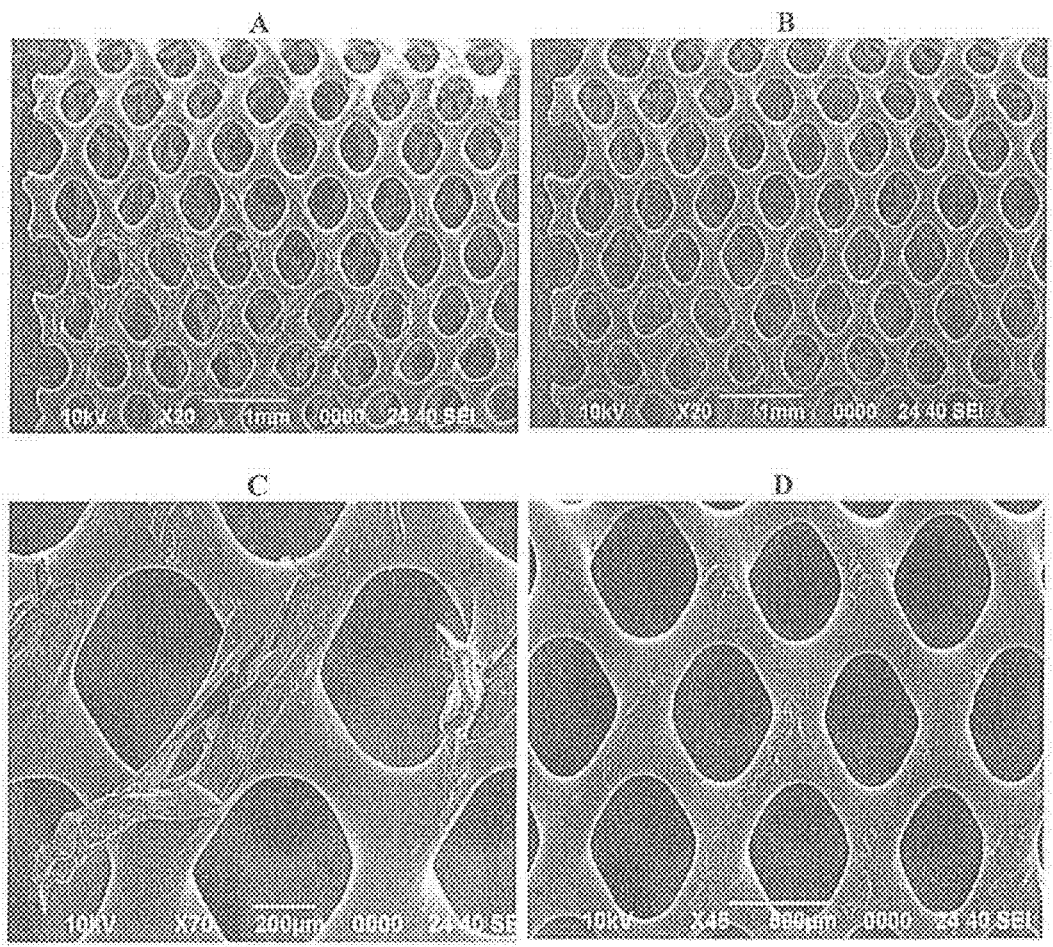
FIG. 8 includes scanning electron micrographs of polymeric implants after loading and unloading with delivery devices according to certain embodiments of the invention.
Figure 17A:
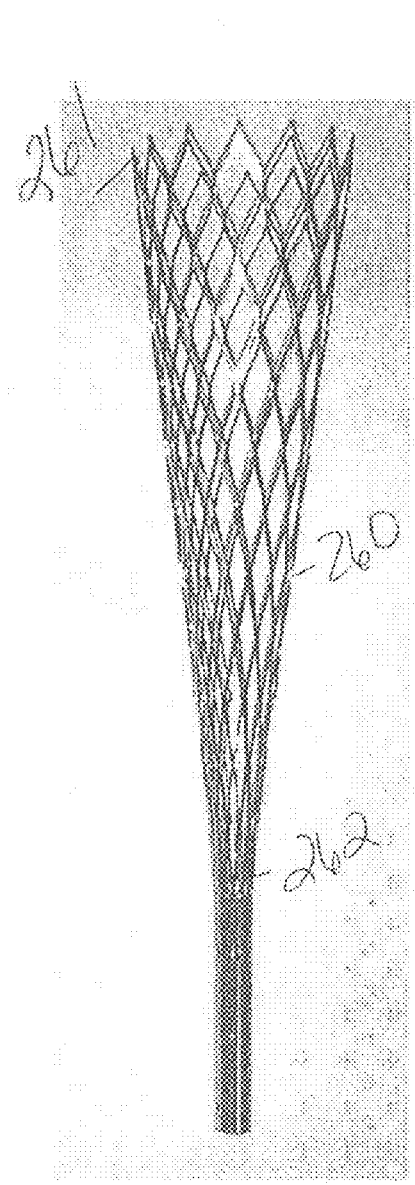
FIGS. 17A and 17B include photographs of expandable members according to embodiments of the invention.
Figure 17B:
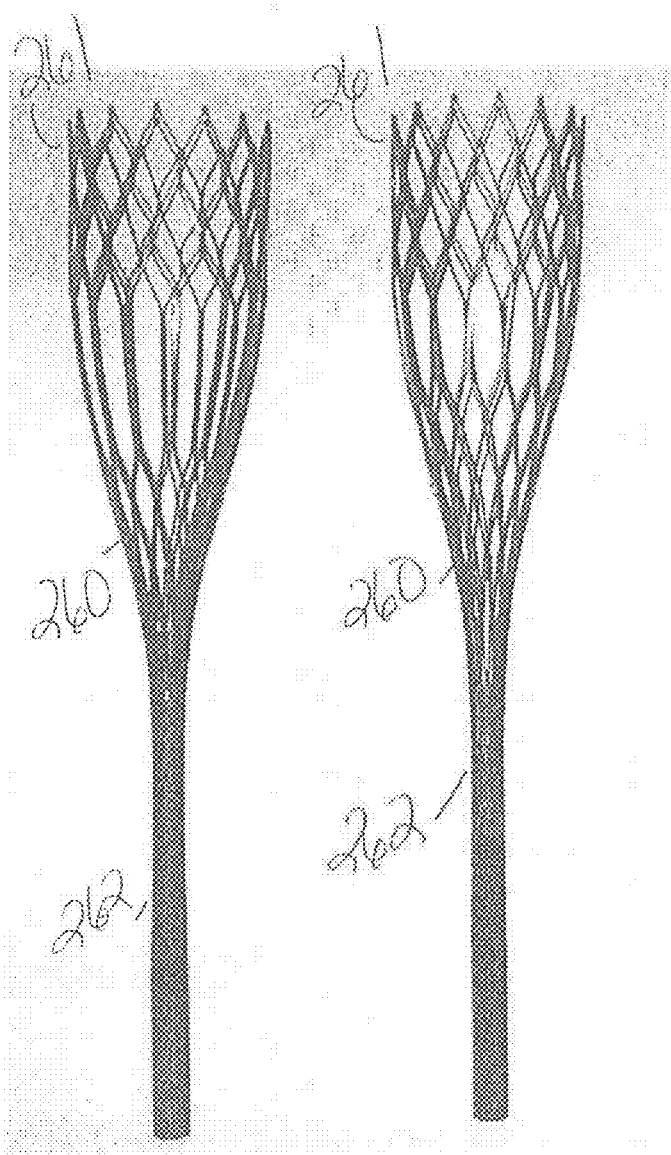
Figure 18B:
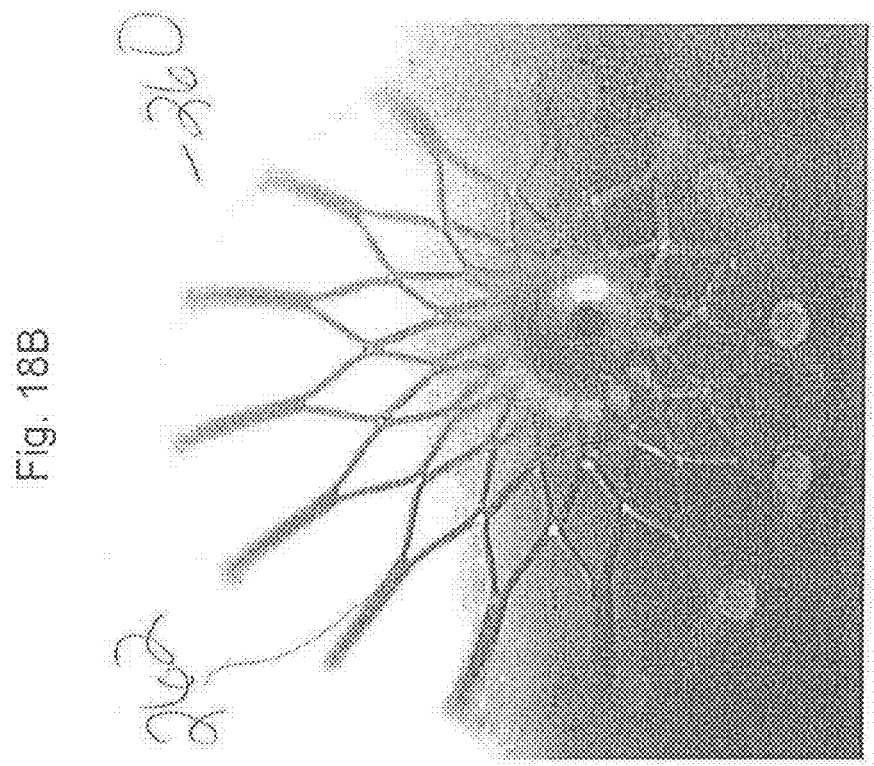
FIGS. 18A and 18B include photographs of expandable members according to embodiments of the invention.
Figure 18A:
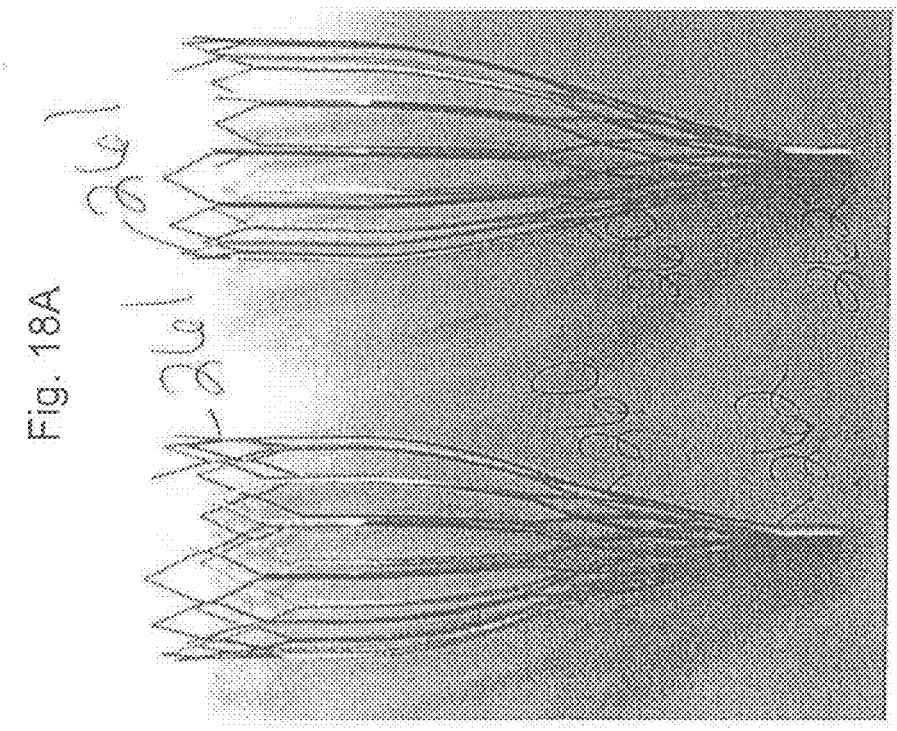

In preferred embodiments, the first expandable member 220 comprises a mesh or woven structure, and at least a portion of the woven/mesh structure includes relatively long, parallel straight members ("struts") as shown in FIGS. 17B and 18A-B. More generally, preferred designs for the first expandable member 220 minimize the degree of contact between angled portions of the mesh or weave of expandable member 220 and fragile portions of the tubular implant 100 (for example, nodes of a woven or mesh implant), thereby minimizing the risk of pinching, deforming or otherwise damaging the tubular implant 100. Inner surfaces of the first expandable member 220 are optionally electropolished, coated or otherwise treated to optimize the degree of friction between the first expandable member 220, further reducing the risk of damage to the tubular implant 100 by reducing the likelihood of catching or slippage during loading. FIG. 8 shows the surfaces of polymeric implants 100 after loading into delivery systems 200 having first expandable members 220 with internal surfaces having varying degrees of electropolishing. As shown in FIGS. 8A and 8C, implants loaded using first expandable members 220 having a low degree of electropolishing demonstrate a relatively high degree of surface abrasion, while implants loaded using first expandable members 220 with a high degree of electropolishing, and a relatively smoother inner surface, exhibit substantially less surface abrasion.

Figure 20:
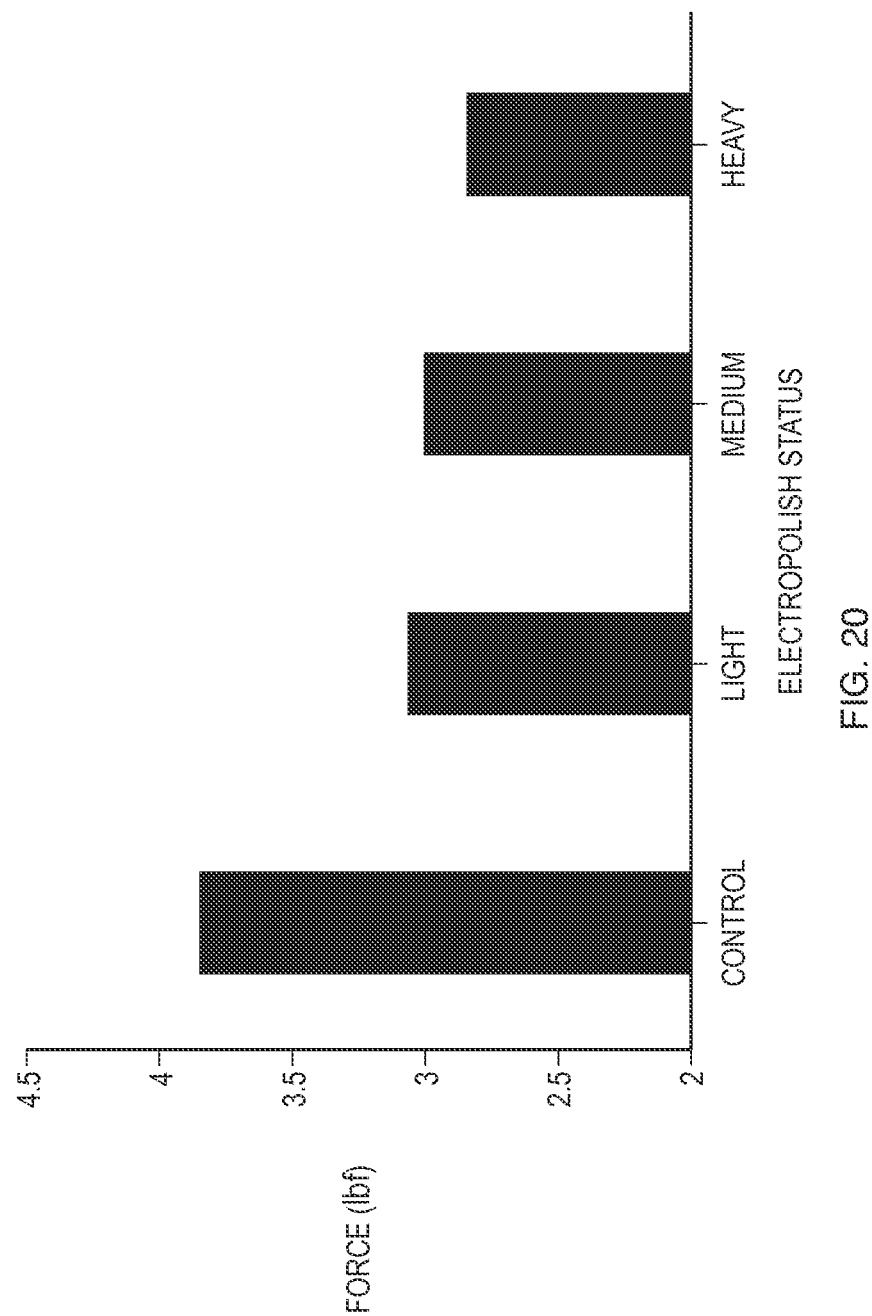
FIG. 20 shows the force in pound-feet required to retract the first expandable member after implant loading in implants in high-medium, low and control electropolishing conditions.

Electropolishing the first expandable member 220 also advantageously reduces the force necessary to retract the first expandable member 220 from the tubular implant 100 after crimping within the outer tubular shaft 240. As the forces which must be applied by and to moving parts of the delivery device 200 are reduced, the risk of mechanical failure, the need to use stronger materials, and the expense of manufacturing the device may all be advantageously reduced. As shown in FIG. 20, the force required to retract the first expandable member 220, as measured on a tensile measuring device, decreases as the degree of electropolishing increases, and the retraction force is lowest in the high electropolishing condition.

While not wishing to be bound to any theory, it is believed that, when mesh or woven structures such as the first expandable member 220 are collapsed in a proximal-to-distal direction, the distal-most elements will tend to elongate as they are collapsed. If the mesh or weave is closed—that is, if the individual strands are fixed to one-another where they cross—the structure may be unable to elongate fully and will instead tend to widen at the distal end (termed "trumpeting"). In preferred embodiments, trumpeting is minimized, and the implant 100 is more efficiently captured and held during crimping, by forming the first expandable member 220 from a mesh or weave in which the strands of the mesh or weave are not attached to one-another at the distal-end of the first expandable member 220, as shown in FIG. 17A. Because the distal-most strands are not connected, they can elongate fully during crimping without trumpeting.

Loading and Delivery

Figure 4:
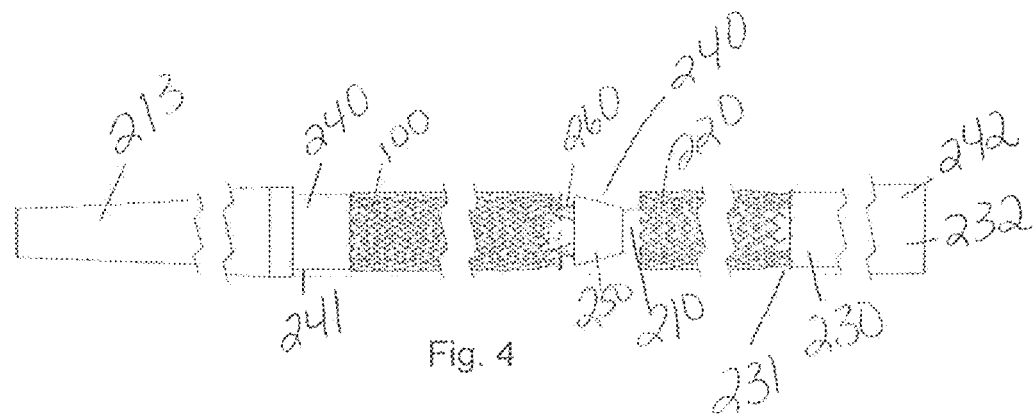
FIG. 4 is a side view of a loaded delivery device, in accordance with an embodiment of the present invention.

To load the delivery system 200 with a polymeric tubular implant 100 outside of a patient's body, the implant 100 (in its unstressed configuration) is advanced over the distal end 211 of the inner shaft 210. In a preferred embodiment, the inner shaft 210 includes an enlarged diameter portion 250 located proximal to the distal end 211. The enlarged diameter portion 250 may be, for example, formed as part of the inner shaft 210 or a ring member or the like that is mounted onto the inner shaft 210. When the enlarged diameter portion 250 is used, the implant 100 is placed between portion 250 and the distal end 211 of the inner shaft 210. When the enlarged diameter portion 250 is not used, the implant 100 is placed at a suitable location along the inner shaft 210 proximal to its distal end 211. The first expandable member 220 is then advanced distally, such as by sliding the tubular middle shaft 230 over the inner shaft 210, so that at least a portion of the implant 100 is located within the open distal end 221 of the first expandable member 220, as shown in FIG. 3. The tubular outer shaft 240 is then advanced distally by sliding it over the inner shaft 210 and/or tubular middle shaft, 230. During the advancement of the tubular outer shaft 240 over the first expandable member 220, the first expandable member 220 applies a radial compressive force to the implant 100, which is crimped into the tubular outer shaft 240 as it is advanced distal to the implant 100 and preferably to the distal end 211 of the inner shaft 210. The tubular outer shaft 240 is advanced to a location at or near the distal end 211 of the inner shaft 210, and if tip 213 is used, the tubular outer shaft 240 is advanced such that it preferably butts against tip 213. The first expandable member 220 is then withdrawn towards the proximal end 212 of the inner shaft 210, such as by withdrawing the tubular middle shaft 230, such that the first expandable member 220 is no longer over any part of the implant 100, as shown in FIG. 4. The use of the enlarged diameter portion 250 may be helpful in withdrawing the first expandable member 220 over the implant 100 when the enlarged diameter portion 250 is sized to function as a stop to prevent the implant from being dragged proximally as the first expandable member 220 is pulled proximally when in contact with the implant 100. Depending upon the materials used for each of the implant 100 and the first expandable member 220, it may also be preferable to apply a lubricious material or coating to the first expandable member 220 to facilitate the ease of withdrawal of the first expandable member 220 over the implant 100.

The delivery system 200 is now ready for insertion into a patient to deliver the implant 100 to a target location. Unlike conventional stent delivery systems that require stent loading as part of the manufacturing and/or packaging processes, the delivery systems of the present invention offers the ability for tubular implants to be loaded by a healthcare professional immediately prior to delivery into a patient. As such, when used with the delivery systems of the present invention and loaded immediately prior to delivery, polymeric implants are not shipped and stored in a crimped configuration and therefore are not likely to undergo stress relaxation. It should be recognized that although the delivery systems of the present invention offer the ability of end-point loading, they are not so limited and may be loaded as part of the manufacturing and/or packaging processes provided that the implant to be delivered is able to withstand shipping and storage while in a crimped configuration and without any adverse effects.

Figure 5:
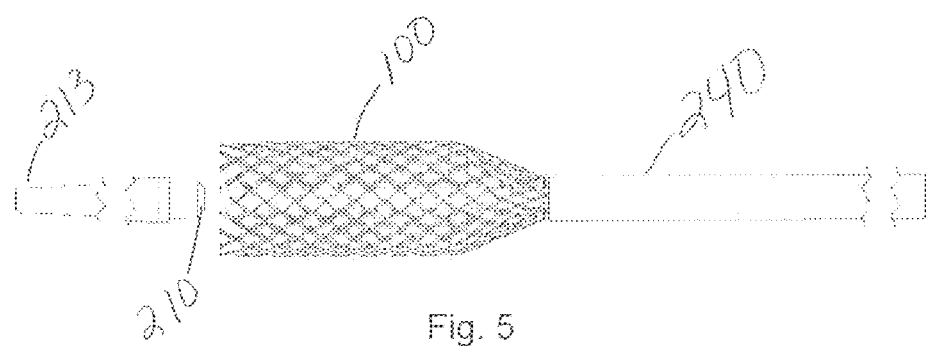
FIG. 5 is a side view of a polymeric tubular implant during delivery using the delivery system of the present invention.

Once the delivery system is advanced to a target location in a patient's body, the outer shaft 240 is then withdrawn in a proximal direction. As the distal end 241 of the outer shaft 240 is withdrawn from over the implant 100, the implant self-expands towards its unstressed configuration as shown in FIG. 5. Once the implant is fully released from its crimped condition, the delivery system 200 is withdrawn from the patient to leave the implant at its desired location.

The Second Expandable Member

In an embodiment of the present invention as shown in FIG. 2, the delivery device includes a second expandable member 260 that is affixed to the inner shaft 240 distally from the first expandable member 220. If enlarged diameter portion 250 is used, the second expandable member 260 is located between the enlarged diameter portion 250 and the distal end 211 of the inner shaft 210. Like the first expandable member 220, the distal end 261 of the second expandable member 260 has a cross-sectional diameter greater than the diameter of the polymeric tubular implant 100 when in an unstressed configuration, and a proximal end 262 having a cross-sectional diameter less than the diameter of the polymeric tubular implant 100 when in an unstressed configuration. Unlike the first expandable member 220, however, the second expandable member 260 does not require an open distal end, although in a preferred embodiment, the distal end 261 of second expandable member 260 is open as shown in FIG. 2.

The second expandable member 260 is a resilient structure that, when not subjected to external stresses, will self-expand to an unstressed configuration such as the configuration shown in FIG. 2. Second expandable member 260 may be made from any suitable metallic or polymeric material, and is preferably a shape memory material such as Nitinol. If second expandable member 260 is not made from a shape memory material, it is made from an otherwise elastic material having a configuration that results in a self-expanding property, such as, for example, spring temper stainless steel or cobalt nickel alloys. Preferably, the first expandable member has a mesh or woven structure, as shown in FIG. 2. In other embodiments, the second expandable member 260 is made from a balloon, foam, or other expanding material.

Figure 6:
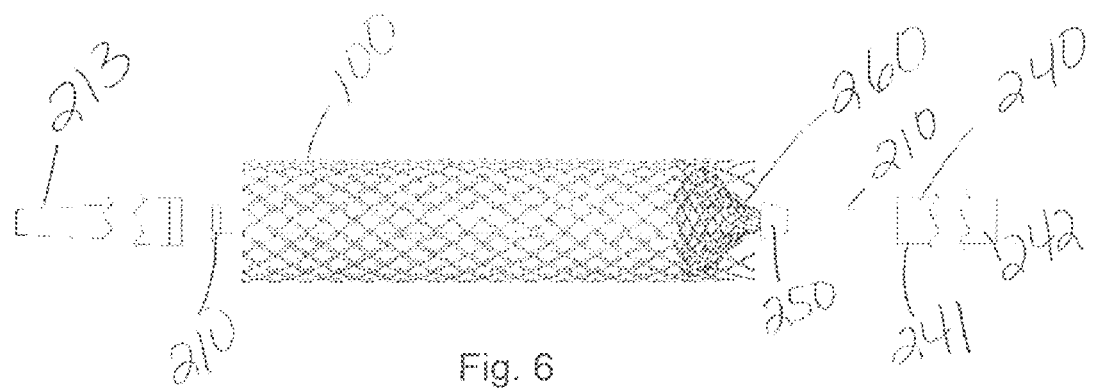
FIG. 6 is a side view of a delivery device during loading of a polymeric tubular implant, in accordance with an embodiment of the present invention.

In use, the implant is placed over the second expandable member 260 prior to crimping, as shown in FIG. 6. When the implant is crimped using the first expandable member 220 and the tubular outer shaft 240, the second expandable member 260 is likewise compressed to a reduced configuration beneath the implant 100, as shown in FIG. 4. Likewise, the second expandable member 260 expands with the polymeric tubular implant 100 when it is released from its crimped configuration. Because the distal end 261 of the second expandable member 260 has a cross-sectional diameter greater than the diameter of the polymeric tubular implant 100 when in an unstressed configuration, the second expandable member 260 applies a force to the inner diameter of the implant 100. This force may help the implant 100 to expand to its desired configuration, and will further prevent a sometimes-occurring phenomenon known as "stent jumping" in which self-expanding implants excessively move or "jump" when they are extruded from their delivery devices. Use of the second expandable member 260 therefore results in an improvement in the controlled delivery of implant 100 when compared with conventional delivery devices of self-expanding medical implants.

When enlarged diameter portion 250 and second expandable member 260 are used with the present invention, the proximal end 261 of the second expandable member 260 preferably has a cross-sectional diameter that is less than that of the enlarged diameter portion 250 so that the enlarged diameter portion 250 can fulfill its intended purpose, as previously described, to prevent the implant from being dragged proximally as the first expandable member 220 is pulled proximally when in contact with the implant 100.

The Soft Tip

Figure 15A:
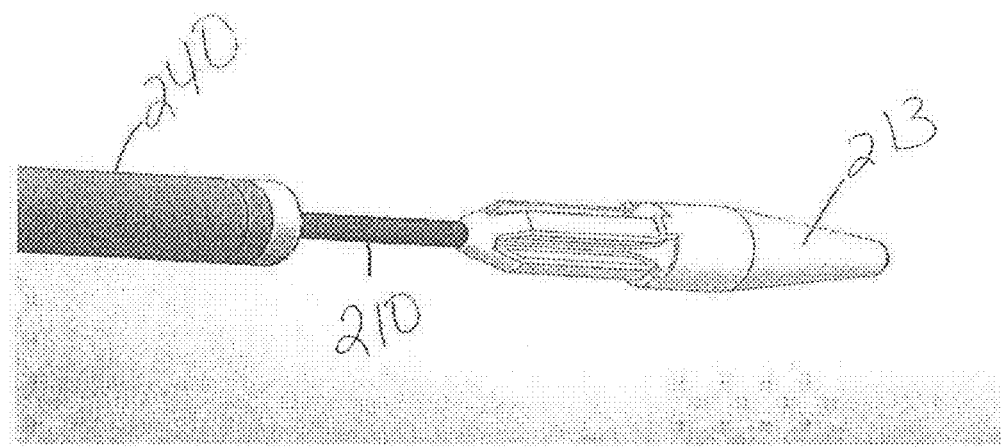
FIG. 15A and FIG. 15B include schematic depictions of a soft tip according to an embodiment of the invention.
Figure 15B:
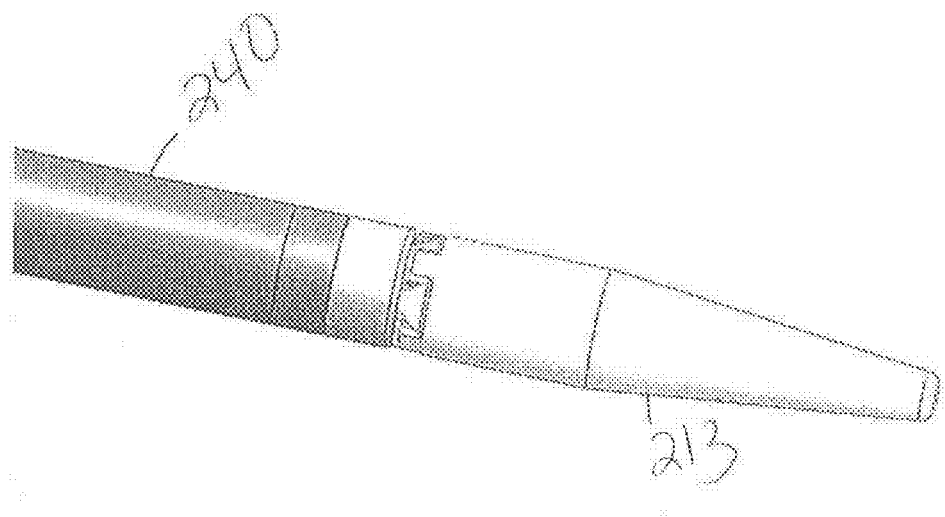

The soft tip 213 is disposed at the distal end 211 of the inner shaft 210 to reduce the risk of trauma or puncture of the walls of a body lumen during a delivery procedure. Soft tip 213 is any suitable shape and is made from any suitable biocompatible material as is known in the art, for instance nylon, silicone, polyurethane or polyether block amide polymers such as Pebax® (commercialized by Arkema Specialty Polyamides, France), and preferably includes a radiopaque marker or a radiopaque filler to enhance the visibility of the soft tip 213 under fluoroscopic visualization. The proximal portion of the soft tip 213 is sized to fit within the lumen of the tubular outer shaft 240, and optionally includes a portion sized to interfit with the open distal end 242 of the tubular outer shaft 240. The interfitting portion is optionally tapered or otherwise shaped to extend into the lumen of the tubular outer shaft 240, as shown in FIG. 15A, and can include one or more scalloped portions or other open spaces that permit fluid to flow through the device 200 and out the tip 213, for instance to allow for flushing of the delivery device 200, as shown in FIG. 15B.

Cushions

Delivery devices of the present invention can, in some embodiments, include features to facilitate loading of implants on delivery devices. In one non-limiting example, delivery system 200 includes a cushion 280 positioned on the inner shaft 210. Cushion 280 can be any suitable shape—for example rectangular, square, triangular or cruciform—and can be made from any suitable material. In preferred embodiments, cushion 280 is made of a compressible or elastic material such as silicone. The inventors have found that silicone formulations that have durometer values of about 40 are particularly well suited for use as cushion materials. Nu-Sil MED4940 (Nu-Sil Technology, Carpinteria, Calif.) is one silicone formulation that may be used in embodiments of the invention.

Cushion 280 may have any suitable dimensions along both the circumference and the long axis of inner shaft 210, which dimensions are selected to achieve satisfactory retention of the tubular implant 100 while minimizing the risk of interference between cushion 280, the tubular implant 100 and the first expandable member 220. In certain embodiments, balancing these elements is achieved by selecting a length for the cushion 280, as measured along the long axis of inner shaft 210, that is less than the length of implant 100. For example, the cushion may have a length of about 20% of the implant, about 30%, about 40%, about 50%, about 60%, about 70%, about 80% about 90%, about 95%, or about 100%. The cushion 280 may extend completely or partially about the circumference of the inner shaft 210. In embodiments where the inner shaft 210 includes an enlarged diameter portion 250, the cushion 280 is located at least partially within the enlarged diameter portion 250, and is preferably located completely within the enlarged diameter portion.

The cushion 280 optionally includes a textured surface to interact with, and thereby help retain, the inner surface of the tubular implant 100. As shown in FIG. 16, one exemplary design includes a plurality of repeating segments, each segment in turn comprising a textured or ribbed surface. The cushion 280 of FIG. 16 includes three repeating segments, and each segment comprises a plurality of repeating rows of cuboid protrusions arranged circumferentially about the cushion 280.

Figure 21:
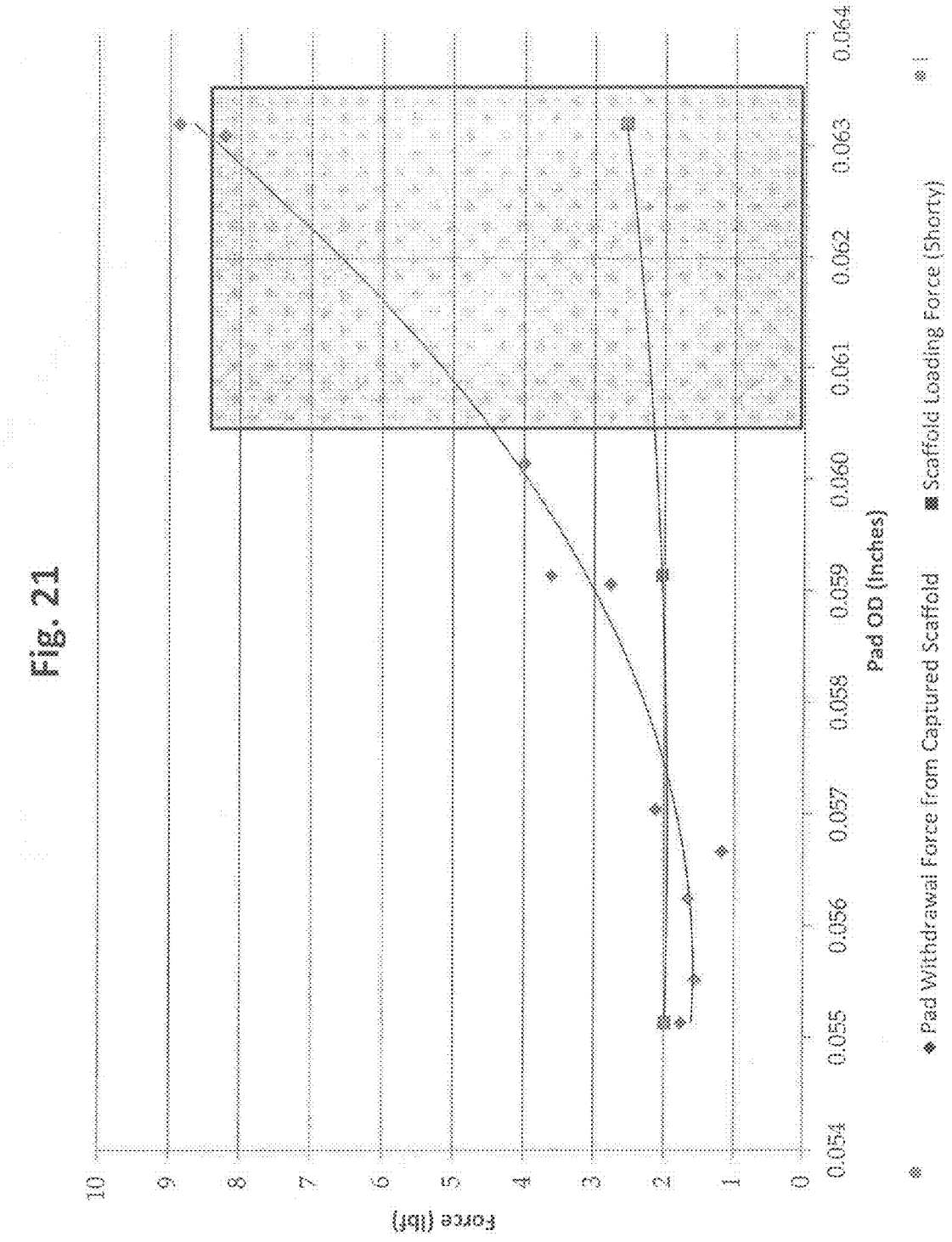
FIG. 21 plots the loading force (lower series) and the withdrawal force (upper series) required for test cushions having varying maximum thicknesses.

Cushion 280 aids retention of implant 100 during loading of delivery device 200 by providing increased surface area on the inner shaft 210 with which to contact the implant as the implant 100 is compressed onto inner shaft 110. Additionally, cushion 280 holds the implant 100 tightly against the inner wall of the outer shaft 240 after loading but resists lateral displacement, preventing retrograde translation of the implant 100 as the outer shaft 240 is retracted during implant delivery. The inventors have found that the use of a cushion 280 having a ribbed surface advantageously, and surprisingly, increases the force necessary to remove or displace the implant 100 when is crimped within the catheter—thereby reducing the risk that the implant will migrate during withdrawal of the tubular outer shaft 240—without significantly increasing the force necessary to load the implant 100 onto the cushion 280. FIG. 21 plots the loading force (lower series) and the withdrawal force (upper series) required for test cushions having varying maximum thicknesses. The upper series shows that, as the maximum thickness of the ribs on the cushion 280 are increased, the force necessary to remove the implant 100, as measured on a tensile tester, increases as, roughly, the square of the rib thickness. By contrast, the force necessary to load the implant 100 onto the cushion 280 is not substantially affected by variations in the thickness of the ribs.

For a delivery device 200 that includes a cushion 280, the loading process proceeds as described above, with the modification that implant 100 is advanced over the cushion 280 prior to crimping. When the implant is crimped using the first expandable member 220 and the tubular outer shaft 240, implant 100, is crimped down onto cushion 280, facilitating its secure positioning and preventing translation of the implant 100 during the loading process.

The cushion 280 is subjected to forces oriented parallel to the inner shaft 210 during the loading and deployment processes, for example by the movement of the inner, middle and outer shafts 210, 230, 240 relative to one another. It may be desirable, therefore, to improve the degree of adhesion or the extent of static friction between the cushion 280 and the inner shaft 210, or to otherwise prevent or limit lateral displacement of the cushion 280 during loading or deployment of the implant 100. In the embodiment shown in FIG. 16, a pad 281 is placed immediately proximal to the cushion 280 along the inner shaft 210. The pad 281 may extend circumferentially about all or part of the inner shaft 210, and acts to secure the portion of the implant 100 that is under the first expandable member 220, while also helping to prevent deformation of the ends of the implant 100 when it is crimped.

Loading Aids

Figure 9:
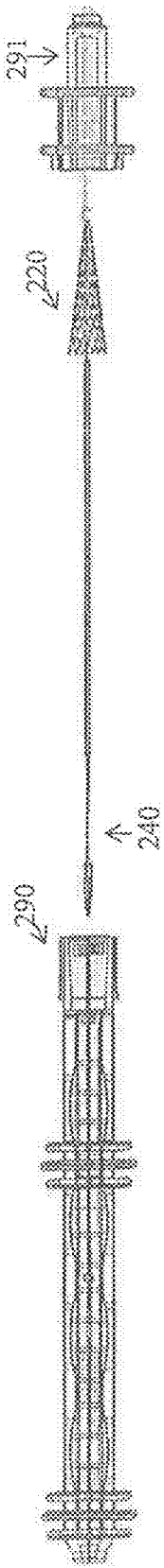
FIG. 9 includes a schematic depiction of a loading aid according to an embodiment of the invention.
Figure 10:
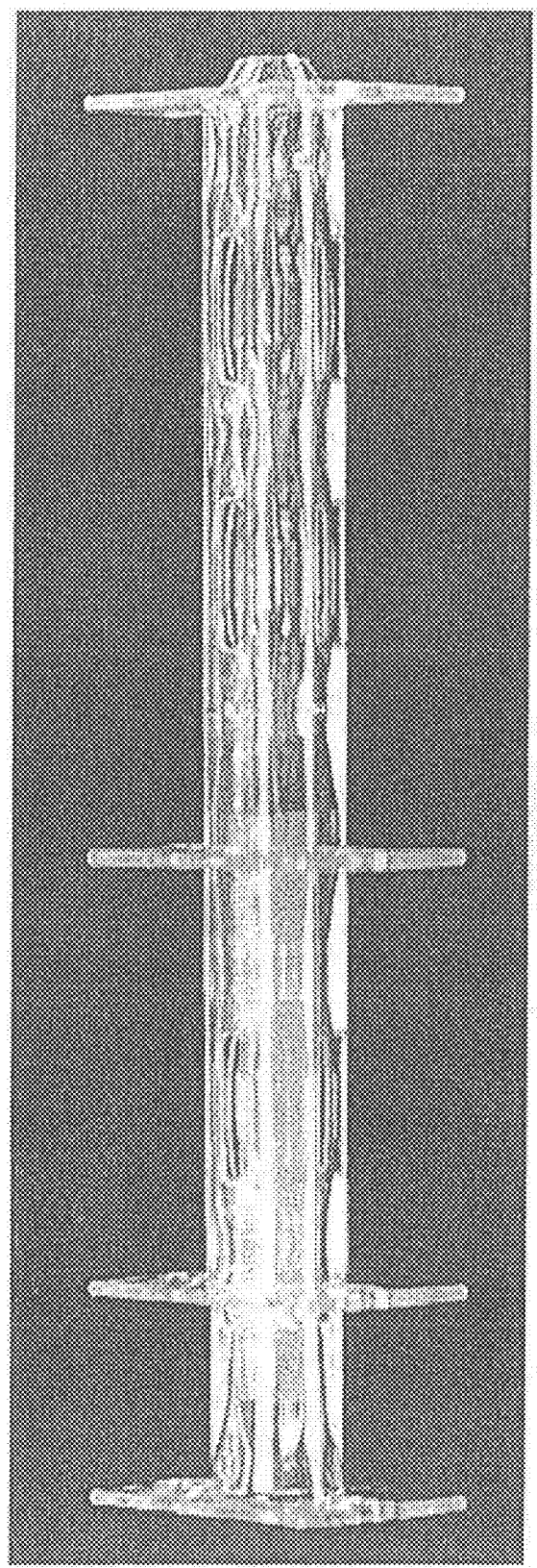
FIG. 10 includes a photograph of a loading aid with a tubular implant disposed inside according to an embodiment the invention FIG. 11 includes a schematic depiction of a distal portion of a delivery device according to an embodiment of the invention.
Figure 11:
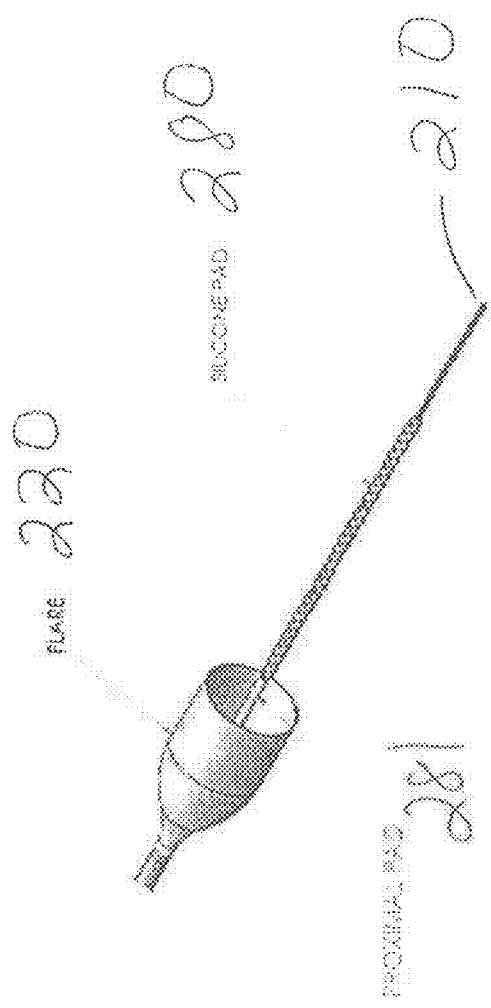

In certain embodiments, systems of the invention include a loading aid 290 that encloses implant 100 in its fully expanded configuration in order to aid loading of the implant 100 onto delivery device 200, as shown in FIG. 9. Loading aid 290 is a generally elongate body having a through-lumen sized to accommodate implant 100 and the first expandable member 220 in its fully expanded configuration. The through-lumen is open to an exterior of the loading aid 290 on at least one end, permitting insertion of the inner shaft 210 of delivery device 200. Preferably, the through lumen is open on both ends to minimize the risk that the distal tip of the delivery device 200 will be damaged by contacting the interior of the loading aid 290 during loading.

Loading aid 290 advantageously does not compress or crimp implant 100, but merely constrains the implant 100 in order to ease its advancement over inner shaft 210. The loading aid 290 may include one or more features to limit migration of implant 100 therewithin. For example, the through lumen may comprise three or more sections, a first section having an inner diameter greater than the outer diameter of the implant 100 and second and third sections which have inner diameters less than the outer diameter of implant 100 and which flank the first section. Alternatively or additionally, the through lumen may include protrusions such as pins, nubs, etc. that interact with the tubular implant 100 to prevent migration thereof.

In use, the inner shaft 210 is inserted into the through lumen of the loading aid 290 in order to advance the implant 100 over the inner shaft 210. The first expandable member 220 is then advanced distally through the through lumen of loading aid 290 so that at least a portion of the implant 100 is located within the open distal end 221 of the first expandable member 220. Loading aid 290 can also include visual aids such as surface markings which demarcate the position of implant 100 within loading aid 290. Additionally, loading aid 290 may include tactile aids within the through lumen, such as regions of reduced inner diameter or textured surfaces on the inner surface of the through lumen which alert a user that the first expandable member 220 has been advanced to the correct position. In some embodiments, the physical dimensions of loading aid 290 are chosen to be complementary to the capabilities of delivery device 200: for example, the distance between an open end of the loading aid 290 and the region which contains the implant 100 may be selected to match with a length of the inner shaft 210 when extended to a known degree, such as 50% of maximum, etc.

In preferred methods, the loading aid 290 is used in conjunction with, and interfits with, a locking collar 291 that is preferably reversibly engageable with the outer shaft 240 of the delivery device 200. The locking collar 291 is interfittable with the loading aid 290 and aids in aligning the distal tip and the inner shaft 210 with the through lumen of the loading aid 290. The locking collar 291 optionally includes a through-lumen that is sized and shaped to help guide the distal tip 210 of the delivery device 200 into position for loading. In particular, as the inner shaft 210 of the delivery device 200 is advanced into the through lumen of the loading aid to the correct position for loading the implant 100 onto the delivery device, the locking collar 291 contacts the loading aid 290, preventing further advancement of the delivery device 200. In some embodiments, the user receives feedback that the loading aid 290 and the locking collar 291 are correctly engaged, for example in the form of an audible click or the appearance of a visual indicator.

The loading aid 290 is preferably formed from two or more pieces so that it can be assembled around the tubular implant 100, avoiding the need to compress the implant 100 during kit assembly.

Controllers

Figure 12:
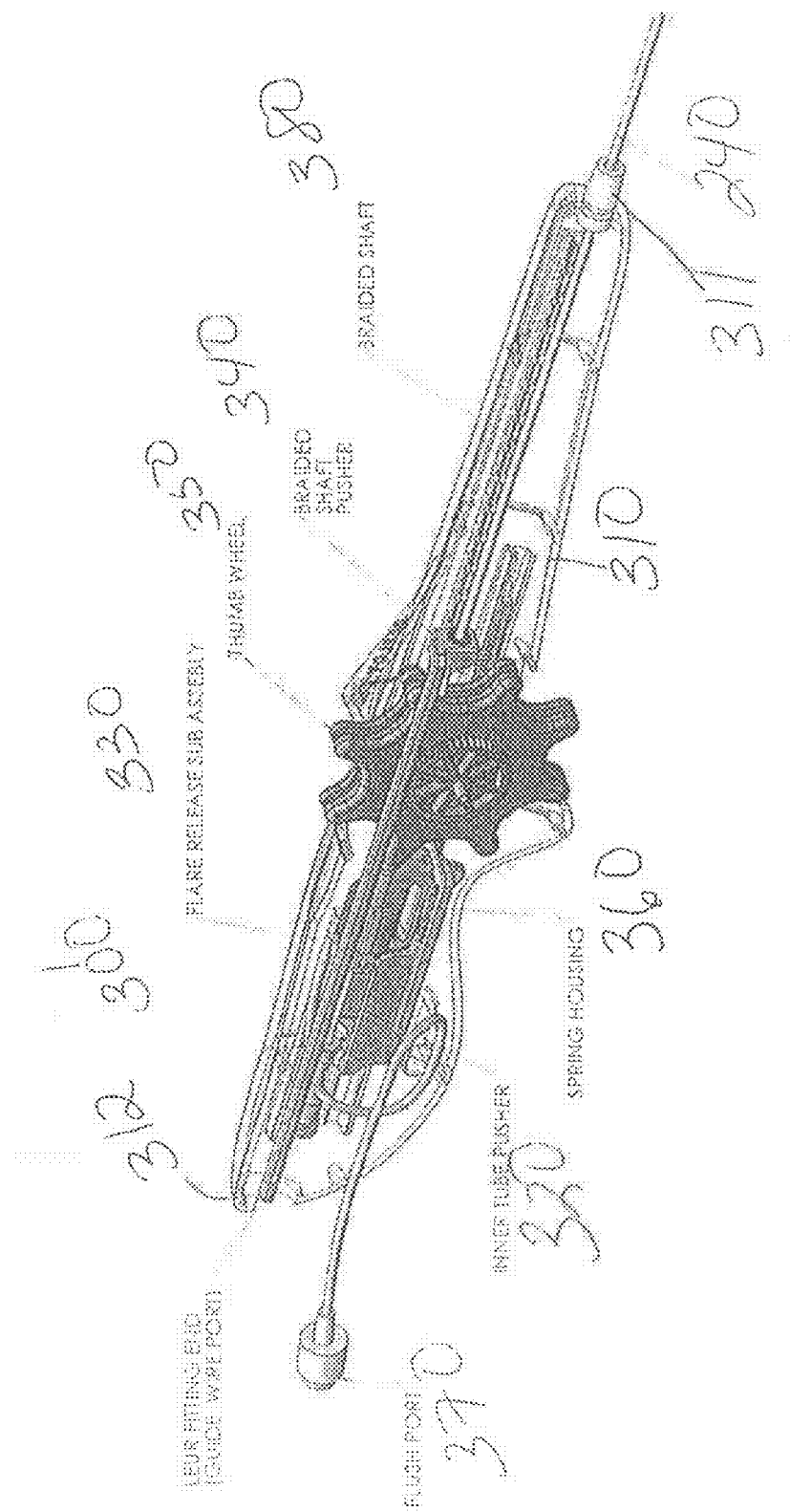
FIG. 12 includes a schematic cutaway view of a handle of a delivery device according to an embodiment of the invention.
Figure 13:
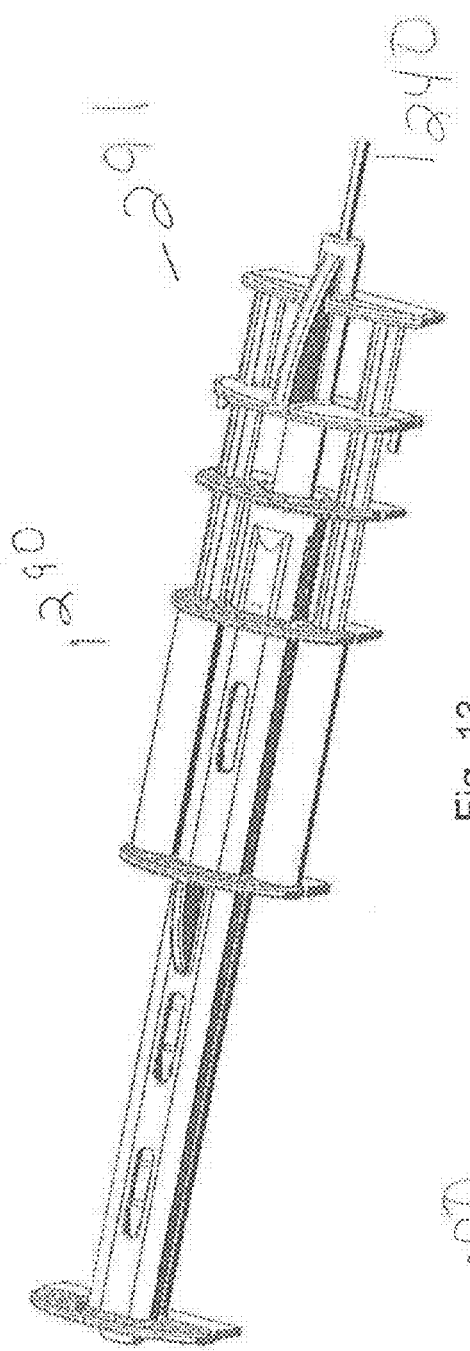
FIG. 13 includes a schematic perspective view of a loading device in use according to an embodiment of the invention.

Delivery devices of the invention generally include controllers disposed at the proximal ends of the devices. Controllers according to the invention are preferably ergonomically shaped and contain simple to use and easy-to-manipulate means for actuating extending and retracting one or more of the inner shaft 210, the first expandable member 220 and/or the middle shaft 230 and the outer shaft 240. For example, in the exemplary controller 300 depicted in FIG. 12, a thumbwheel 350 is used to control the positions of each of the inner shaft 210, the first expandable member 220, and the outer sheath 240 relative to one-another. The controller 300 includes a proximal end 311 and a distal end 312, as well as a flush port 370 that is fluidly connected to the lumen of one or more of the outer and middle sheaths 240, 230.

The thumbwheel 350 advantageously permits a user to control the relative positions of all three of the inner shaft 210, outer shaft 240 and the first expandable member 220 relative to one-another. In preferred embodiments, the ratio of advancement of the inner shaft 210 to the retraction of the outer shaft 240 is 1:4, permitting the tubular implant 100 to be foreshortened—to assume a configuration in which it has a relatively short length and a relatively large diameter—in advance of its transition from the small-diameter crimped configuration in which it resides while in the delivery device 200 to the larger-diameter open configuration in which it will reside when implanted.

Kits

The present invention includes kits that include the delivery system 200 or the components thereof. In one embodiment, the kit includes a delivery system having an inner shaft 210, a tubular middle shaft having a first expandable member 220 attached thereto, and a tubular outer shaft 240, which may be packaged as separate components or pre-assembled as described herein. An implant 100 may be kitted in the same packaging with the delivery system 200, or may be provided separately.

Figure 7A:
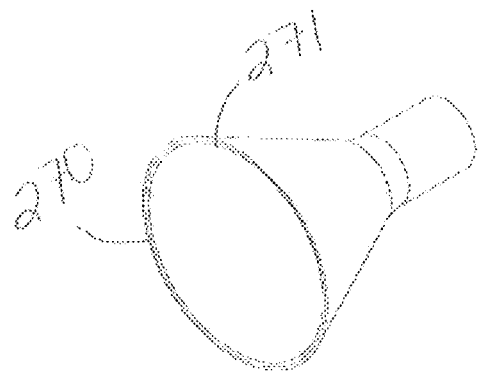
FIGS. 7a and 7 show an optional funnel for use with the delivery system of the present invention.
Figure 7:
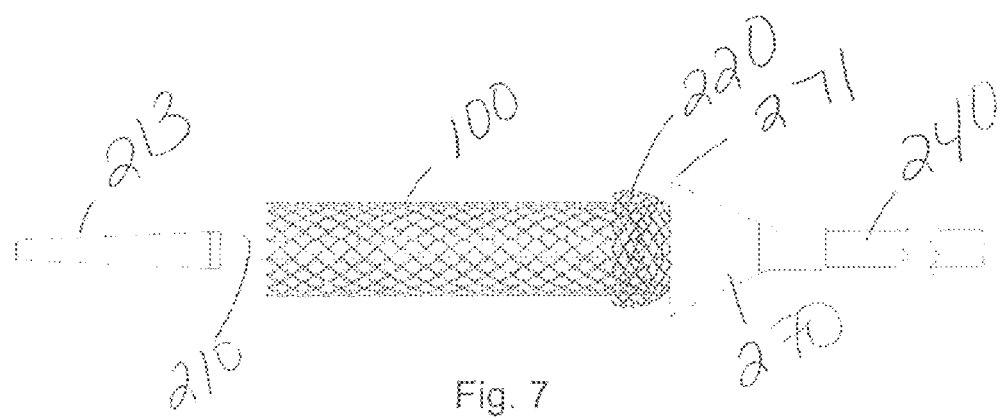
Figure 14:
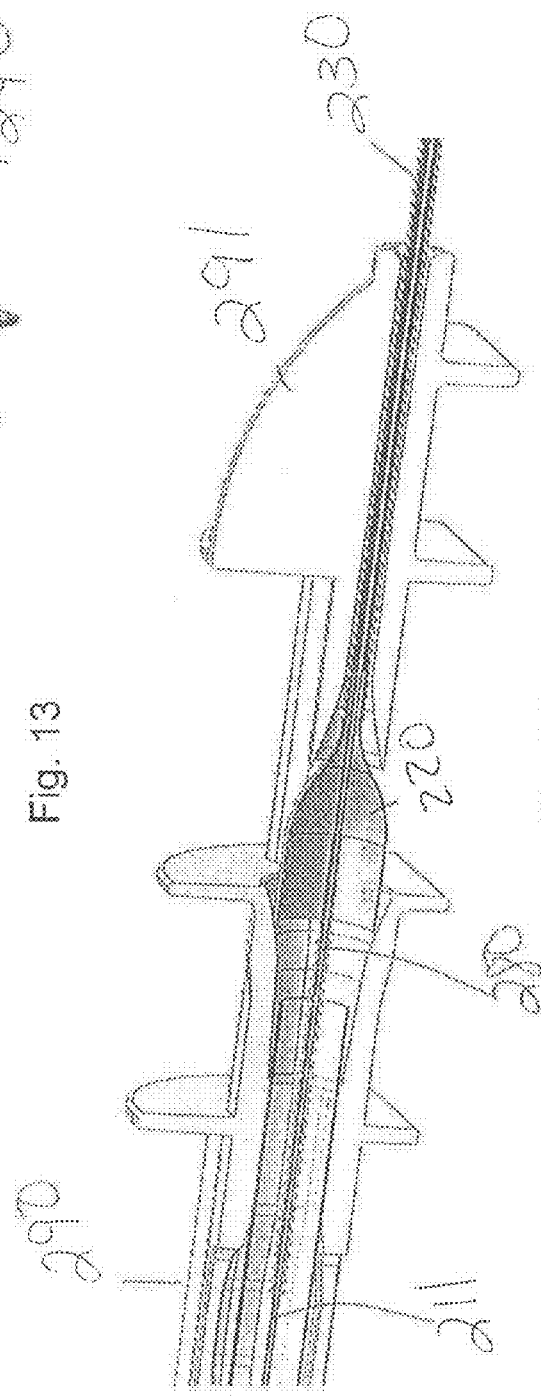
FIG. 14 includes a schematic cutaway view of a loading device in use according to an embodiment of the invention.

Kits of the present invention may also include an optional funnel 270 which is detachably connectable to the distal end of the tubular outer shaft 240 as shown in FIGS. 7a and 7b. Funnel 270 is made from any suitable material, and is preferably a low friction material such as FEP or PTFE. The cross-sectional dimension of distal end 271 of funnel 270 is greater than the diameter of the implant 100 in its unstressed configuration. During loading of the implant 100 into the delivery system 200, funnel 270 may be useful in drawing the first expandable member 220 and implant 100 to within the tubular outer shaft 240. To achieve this purpose, funnel 270 is placed over the proximal end 242 of the outer shaft 240 and advanced to the distal end 241, the outer shaft 240 is moved relative to the tubular middle shaft 230, the inner shaft 210, and the implant 100 to place the first expandable member 220 and implant 100 within the tubular outer shaft 240, and the funnel 270 is then removed from the outer shaft 240 by sliding over either of its distal or proximal ends 241, 242. In some embodiments, such as the one shown in FIG. 14, the funnel 270 is integrated into the collar 291 and/or the loading aid 290 in the form of a region having a tapering inner diameter, which aids compression of the implant during loading.

Figure 19:
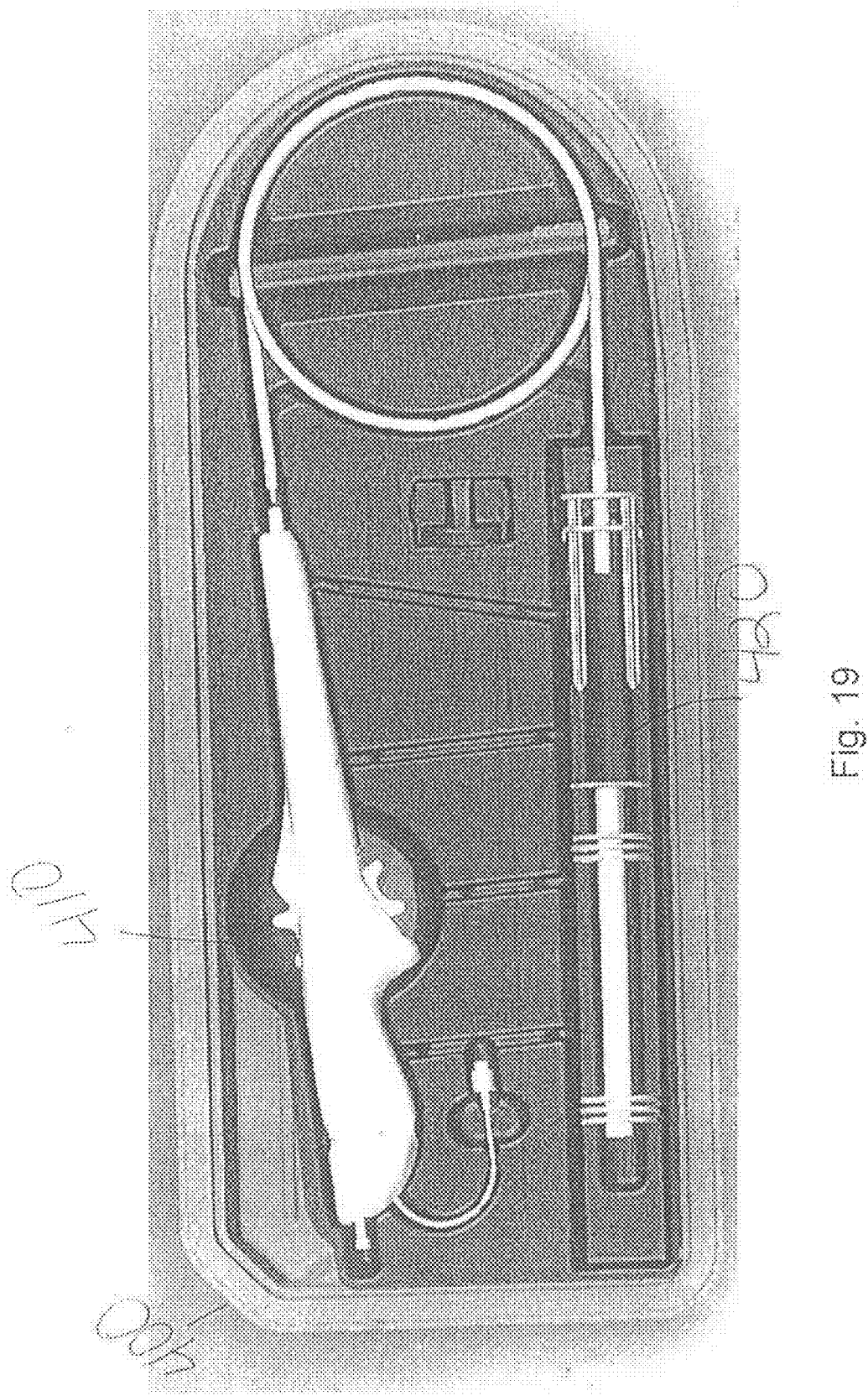
FIG. 19 includes a schematic depiction of a kit according to an embodiment of the invention.

In preferred embodiments, kits of the invention are provided in a format that simplifies loading and use for end users. In the kit shown in FIG. 19, the delivery device 200 and loading aid 290 with implant 100 are provided in a sterile or sterilizable single use tray 400. The tray 300 includes a plurality of voids or compartments 410, 420 sized to fit the proximal end 212 and the handle, outer shaft 240, distal tip and loading aid in a configuration that minimizes the stress on the inner, middle and outer shafts 210, 230, 240. Among other things, the compartments are sized and shaped to avoid coiling the shafts too tightly, thereby preventing kinking during storage.

The distal tip of the delivery device 200 is preferably engaged with the locking collar 291 and kitted in the same compartment as the loading aid 290, and the compartment 410 is preferably sized and shaped to permit the distal tip and the locking collar 291 to engage with the loading aid 290 while at least part of the delivery device 200 remains in the tray 400. In the kit shown in FIG. 19, the compartment 410 is elongated, and positions the distal tip, locking collar 291 and loading aid 290 along the same axis, and is shaped to permit a user to slide the loading aid 290 toward the locking collar 291 or vice versa so that the loading aid 290 engages the locking collar 291 and aligns the distal tip with the central axes of the loading aid 290 and the tubular implant 100. The compartment 410 is preferably sized to permit a portion of the device, particularly the distal end 211 of the inner shaft, to extend through the loading aid 290 during the loading procedure without contacting a surface of the tray 400.

The handle and proximal end 212 of the device 200 are contained in another compartment 420, and the device 200 is preferably kitted so that the handle can be manipulated by a user without removing the rest of the device 200 from the tray 400, and without applying excessive stress the inner, middle or outer shafts 210, 230, 240.

The tray 400 is made from a material that can be sterilized after kit assembly, for example by steam or ethylene oxide sterilization. In preferred embodiments, the tray 400 comprises polyethylene terephthalate, and is sealed with a peel-away membrane comprising flashspun high density polyethylene fibers (for example, Tyvek®, E.I. du Pont de Nemours & Co., Wilmington, Del.). The tray 400 comprises two nested layers, an outer layer that is sealed and sufficiently impermeable to maintain the sterility of the contents of the tray 400, and an inner layer that can be lifted out of the outer tray and transferred to a sterile field.

Kits according to these embodiments of the invention advantageously permit end users to rapidly load polymeric implants onto delivery devices in suite and within the trays in which the kits are provided, thus avoiding the potential for deformation due to fatigue that exists when devices are pre-loaded, while also minimizing procedure times.

CONCLUSION

The phrase "and/or," as used herein should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used in this specification, the terms "substantially," "about," or "approximately" mean plus or minus 10% (e.g., by weight or by volume), and in some embodiments, plus or minus 5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

The present invention provides devices, methods, and kits used to deliver polymeric tubular implants to patients in need thereof without undue risk of damaging the implant during the delivery process. While aspects of the invention have been described with reference to example embodiments thereof, it will be understood by those skilled in the art that various changes in form and details may be made therein without departing from the scope of the invention.

We claim:

1. A kit, comprising:
   a tray defining an elongate space;
   a loading aid slidably disposed within the elongate space, the loading aid having a through lumen;
   a tubular implant disposed within the through lumen of the loading aid, the tubular implant being in an unstressed configuration characterized by a first diameter less than an inner diameter of the through lumen and being compressible into a crimped configuration characterized by a second outer diameter; and
   a delivery catheter, comprising:
      an inner shaft having a distal end configured for insertion into a patient, and a proximal end configured to remain outside of the patient when the distal end is inserted into the patient, wherein (i) at least a portion of the inner shaft has a diameter less than the first diameter of the tubular implant and (ii) the inner shaft includes a compliant cushion disposed near the distal end;
      a first expandable member slidably disposed about the inner shaft, the first expandable member comprising an open distal end having a cross-sectional dimension greater or equal to than the first diameter of the tubular implant, the open distal end of the first expandable member being configured for placement therein of at least a portion of the tubular implant in the unstressed configuration, the first expandable member comprising a proximal end having a cross-sectional dimension less than the first diameter of the tubular implant; and
      an outer sheath slidably disposed over each of the inner shaft and the first expandable member,
   wherein the distal end of the delivery catheter is disposed within the elongate space, and each of the inner shaft, the through lumen of the loading aid, and the tubular implant lie on a single axis.

2. The kit of claim 1, further comprising a collar adapted to interfit with the loading aid, the collar being (i) reversibly attached to a portion of the delivery catheter, and (ii) disposed within the elongate space.

3. The kit of claim 2, wherein the delivery catheter further comprises a handle configured to extend and retract at least one of the inner shaft and the expandable member, the handle being disposed within a second space in the tray, the second space being positioned such that removing the handle from the second space does not displace the distal tip within the elongate space.

4. The kit of claim 2, wherein the loading aid, the collar, and the elongate space have substantially the same width.

5. A method of loading an implant onto a delivery catheter, comprising the steps of:
   providing a kit according to claim 2;
   connecting, within the elongate space, the loading aid, the catheter and the collar;
   advancing the inner shaft and the first expandable member into the through-lumen of the loading aid such that at least a portion of the tubular implant is within the first expandable member and the inner shaft extends through a lumen of the tubular implant;
   advancing the outer sheath over the first expandable member and the tubular implant, thereby crimping the tubular implant into the compressed configuration about the inner shaft.

6. The method of claim 5, further comprising the step of removing the distal tip of the delivery device from the loading aid and the collar.

7. The method of claim 5, wherein the step of advancing the inner shaft includes positioning the cushion within the lumen of the tubular implant.

8. The kit of claim 1, wherein the cushion is disposed about the inner shaft, the cushion comprising a compliant material and having a repeating pattern of protrusions.

9. The kit of claim 8, wherein the cushion has a length that is between about 20% and about 80% of a length of the implant.

10. The kit of claim 9, wherein the distal end of the first expandable member includes a region having a constant diameter greater than the first diameter.

11. The kit of claim 10, wherein the first expandable member comprises a mesh or woven material characterized by nodes where structural elements of the mesh or woven material intersect or overlap, and wherein a node density in the proximal portion of the first expandable member is greater than a node density within the constant diameter region.

12. A system for treating a patient, comprising:
    a loading aid having a through lumen open to an exterior of the loading aid on at least one side;
    a tubular implant disposed within the through-lumen of the loading aid in an uncompressed configuration characterized by a first diameter, the tubular implant being compressible into a crimped configuration characterized by a second diameter less than the first diameter; and
    a delivery catheter, comprising:
       an inner shaft having a distal end configured for insertion into a patient and a proximal end configured to remain outside of the patient, wherein (i) at least a portion of the inner shaft has a diameter less than the first diameter of the tubular implant, and (ii) the inner shaft includes a compliant cushion disposed near the distal end;
       a first expandable member slidably disposed about the inner shaft, the first expandable member comprising an open distal end having a cross sectional diameter greater than or equal to the first diameter of the tubular implant, the open distal end being configured for placement therein of at least a portion of the tubular implant in the unstressed configuration, the first expandable member comprising a proximal end having a cross sectional dimension less than a first diameter of the implant; and
       an outer sheath slidably disposed over each of the inner shaft and the first expandable member,
    wherein the through lumen of the loading aid is sized to permit insertion of the distal end of the inner shaft and to permit engagement of the first expandable member with the tubular implant.

13. The system of claim 12, wherein the first expandable member includes a mesh or a woven material, and where individual portions of the mesh intersect but are not connected to one another at the distal end of the first expandable member.

14. The system of claim 12, wherein the distal end of the first expandable member includes a region having a substantially constant diameter.

15. The system of claim 12, wherein an inner surface of the first expandable member is polished.

16. The system of claim 12, wherein the cushion is ribbed.

\* \* \* \* \*